(12) United States Patent
Rothstein

(10) Patent No.: US 9,629,719 B2
(45) Date of Patent: Apr. 25, 2017

(54) DELIVERY SYSTEMS AND METHODS OF IMPLANTATION FOR PROSTHETIC HEART VALVES

(75) Inventor: Paul Rothstein, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 335 days.

(21) Appl. No.: 13/091,672

(22) Filed: Apr. 21, 2011

(65) Prior Publication Data

US 2011/0264191 A1    Oct. 27, 2011

Related U.S. Application Data

(60) Provisional application No. 61/327,222, filed on Apr. 23, 2010.

(51) Int. Cl.
*A61F 2/24* (2006.01)
*A61F 2/95* (2013.01)
*A61F 2/966* (2013.01)

(52) U.S. Cl.
CPC .......... *A61F 2/2436* (2013.01); *A61F 2/2418* (2013.01); *A61F 2002/9505* (2013.01); *A61F 2002/9517* (2013.01); *A61F 2002/9665* (2013.01)

(58) Field of Classification Search
CPC .................. A61F 2/2436; A61F 2/2418; A61F 2002/9505; A61F 2002/9517; A61F 2002/9665; A61F 2/2439; A61F 2/2427; A61F 2/9511
USPC ....... 606/108, 205–209; 623/1.11, 1.12, 2.11
See application file for complete search history.

(56) References Cited

U.S. PATENT DOCUMENTS

| | | | |
|---|---|---|---|
| 3,671,979 A | 6/1972 | Moulopoulos | |
| 4,056,854 A | 11/1977 | Boretos et al. | |
| 4,994,077 A | 2/1991 | Dobben | |
| 5,332,402 A | 7/1994 | Teitelbaum et al. | |
| 5,370,685 A | 12/1994 | Stevens | |
| 5,397,351 A | 3/1995 | Pavcnik et al. | |
| 5,413,586 A * | 5/1995 | Dibie et al. | 606/200 |
| 5,538,008 A * | 7/1996 | Crowe | 600/564 |
| 5,554,185 A | 9/1996 | Block et al. | |
| 5,855,601 A | 1/1999 | Bessler et al. | |
| 6,099,550 A * | 8/2000 | Yoon | 606/205 |
| 6,168,614 B1 | 1/2001 | Andersen et al. | |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

Anderson, J. R., et al., "Transluminal Catheter Implantation of New Expandable Artificial Cardiac Valve", EUR Heart J., 1990, 11: (Suppl) 224a.

Block P C, "Clinical and Hemodyamic Follow-Up After Percutaneous Aortic Valvuloplasty in the Elderly", The American Journal of Cardiology, vol. 62, Oct. 1, 1998.

(Continued)

*Primary Examiner* — Kathleen Holwerda

(57) ABSTRACT

A delivery system for delivery of an implantable stented device to a body lumen that includes an elongated member having a distal tip and a proximal end portion, a wire connection member positioned between the distal tip and proximal end portion of the elongated member, and a plurality of capturing wires extending from a distal end of the wire connection member. Each of the capturing wires includes a distal end having a lower portion that is moveable relative to an upper portion between an open position and a closed position, and a slot defined by the upper and lower portions when they are in the closed position.

15 Claims, 14 Drawing Sheets

(56) References Cited

U.S. PATENT DOCUMENTS

| | | | |
|---|---|---|---|
| 6,241,738 B1* | 6/2001 | Dereume | A61B 17/00234 606/108 |
| 6,506,205 B2* | 1/2003 | Goldberg et al. | 606/200 |
| 6,866,669 B2* | 3/2005 | Buzzard et al. | 606/108 |
| 7,344,553 B2* | 3/2008 | Opolski et al. | 606/207 |
| 7,727,270 B2* | 6/2010 | Rucker | 623/1.11 |
| 7,993,362 B2* | 8/2011 | Lowe et al. | 606/200 |
| 2003/0199963 A1 | 10/2003 | Tower et al. | |
| 2003/0199971 A1 | 10/2003 | Tower et al. | |
| 2004/0034411 A1 | 2/2004 | Quijano et al. | |
| 2004/0236406 A1 | 11/2004 | Gregorich | |
| 2005/0055046 A1* | 3/2005 | McGuckin et al. | 606/200 |
| 2005/0143809 A1* | 6/2005 | Salahieh et al. | 623/2.11 |
| 2005/0187616 A1* | 8/2005 | Realyvasquez | 623/2.11 |
| 2006/0259119 A1* | 11/2006 | Rucker | 623/1.11 |
| 2007/0186933 A1* | 8/2007 | Domingo et al. | 128/207.15 |
| 2008/0262592 A1* | 10/2008 | Jordan | A61F 2/95 623/1.11 |
| 2009/0192586 A1* | 7/2009 | Tabor et al. | 623/1.11 |
| 2011/0257734 A1* | 10/2011 | Chalekian | A61F 2/2433 623/2.11 |

OTHER PUBLICATIONS

Bonhoeffer, et al, "Percutaneous Insertion of the Pulmonary Valve," Journal of the American College of Cardiology (United States), May-15, 2002, pp. 1664-1669.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Steps Toward Percutaneous Aortic Valve Replacement," Circulation (United States), Feb. 12, 2002, pp. 775-778.

Boudjemline, et al, "Percutaneous Implantation of a Valve in the Descending Aorta in Lambs," European Heart Journal (England), Jul. 2002, pp. 1045-1049.

Cribier, A. et al, "Percutaneous Transcatheter Implantation of an Aortic Valve Prosthesis for Calcific Aortic Stenosis: First Human Case Description," Circulation (2002) 3006-3008.

Hilbert S. L., "Evaluation of Explanted Polyurethane Trileaflet Cardiac Valve Prosthesis", J Thorac Cardiovascular Surgery, 1989; 94:419-29.

Kulkinski, D., "Future Horizons in Surgical Aortic Valve Replacement: Lessons Learned During the Early Stages of Developing a Transluminal Implantation Technique", ASAIO J, 2004; 50:364-68.

* cited by examiner

DELIVERY SYSTEMS AND METHODS OF IMPLANTATION FOR PROSTHETIC HEART VALVES

PRIORITY CLAIM

This application claims the benefit of U.S. Provisional Patent Application Ser. No. 61/327,222, filed Apr. 23, 2010, and titled "DELIVERY SYSTEMS AND METHODS OF IMPLANTATION FOR PROSTHETIC HEART VALVES", the entire disclosure of which is incorporated herein by reference.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Implantation of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously-delivered prosthetic heart valves have been suggested having a generally similar configuration, such as by Bonhoeffer, P. et al., "Transcatheter Implantation of a Bovine Valve in Pulmonary Position." Circulation, 2000; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a continued desire to provide different designs of delivery systems that can be used to implant valves in a minimally invasive and percutaneous manner. There is also a continued desire to be able to reposition and/or retract the valves once they have been deployed or partially deployed in order to ensure optimal placement of the valves within the patient.

SUMMARY

Replacement heart valves that can be used with delivery systems of the invention each include a stent or support frame within which a valve structure can be attached. The stents used with delivery systems and methods of the invention include a wide variety of structures and features that can be used alone or in combination with other stent features to achieve a desired result. In particular, these stents can provide a number of different docking and/or anchoring structures that are conducive to percutaneous delivery thereof. Many of the stent structures are thus compressible to a relatively small diameter for percutaneous delivery to the heart of the patient, and then are expandable either via removal of external compressive forces (e.g., self-expanding stents), or through application of an outward radial force (e.g., balloon expandable stents). The devices delivered by the delivery systems described herein can also be used to deliver stents, valved stents, or other interventional devices such as ASD (atrial septal defect) closure devices, VSD (ventricular septal defect) closure devices, or PFO (patent foramen ovale) occluders.

Methods of the invention for insertion of replacement heart valves include the use of delivery systems that can maintain stent structures in their compressed state during their insertion and allow or cause the stent structures to radially expand once they are in their desired location. In particular, the methods of implanting a stent in accordance with the invention can include the use of delivery systems having a plurality of wires, each of which includes a distal end with a slot for capturing a crown or other structural feature of a stent. Each end can further include a moveable flap or extension that helps to hold the stent crown within the slot to allow for positive, consistent release of the stent from the delivery system without the associated complications that can be caused by incomplete release and/or sticking that can occur with other delivery systems.

Delivery systems and methods of the invention can include features that allow the stents to be retrieved for removal or relocation thereof after they have been deployed or partially deployed from the stent delivery systems. The methods of the invention may include implantation of the stent structures using either an antegrade or retrograde approach. Further, in many of the delivery approaches of the invention, the stent structure is rotatable in vivo to allow the stent structure to be positioned in a desired orientation.

BRIEF DESCRIPTION OF THE DRAWINGS

The present invention will be further explained with reference to the appended Figures, wherein like structure is referred to by like numerals throughout the several views, and wherein.

DETAILED DESCRIPTION

As referred to herein, the prosthetic heart valves used in accordance with the various devices and methods of heart valve delivery of the invention may include a wide variety of different configurations, such as a prosthetic heart valve having tissue leaflets or a synthetic heart valve having polymeric, metallic, or tissue-engineered leaflets, and can be specifically configured for replacing any heart valve. That is, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example. Further, while much of the description herein refers to a transcatheter valve delivery system, the delivery system can alternatively be used as an apical delivery system.

Figure 10:
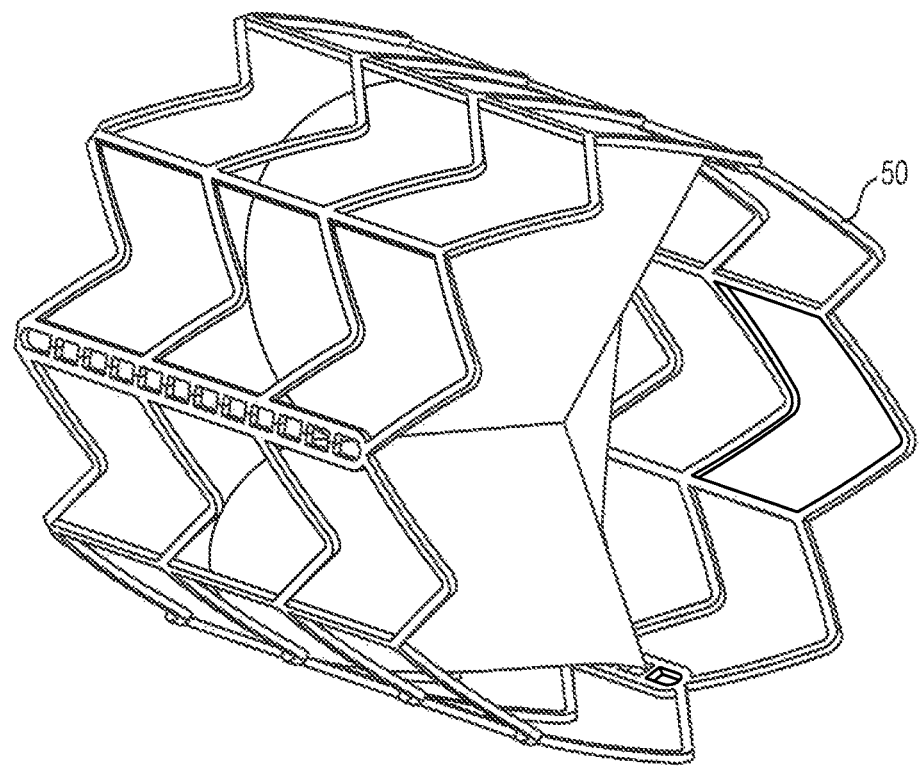
FIG. 10 is a perspective view of a valved stent of the type that can be delivered by the delivery systems of the invention.

Each of the valves used with the delivery devices and methods described herein can include leaflets attached within an interior area of a stent, such as a stent 50 of the type that is illustrated in FIG. 10, which includes a valve mounted with three leaflets within its interior opening. This leaflet configuration is exemplary, and it is noted that leaflets are not shown in many of the illustrated embodiments herein in order to provide a better view of the features of the delivery systems of the invention. In general, the stents used with the delivery systems and methods described herein include a support structure comprising a number of strut or wire portions arranged relative to each other to provide a desired compressibility and strength to the heart valve. Although a number of different configurations of stents can be used, in general terms, the stents described herein are generally tubular or cylindrical support structures, although the diameter and shape can vary along the length of the stent.

Valve leaflets can be secured within the internal area of one of the support structures to provide a valved stent. The leaflets can be formed from a variety of materials, such as autologous tissue, xenograph material, or synthetics, as are known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled to the support structure of the stent. In another alternative, the stent structure and leaflets can be fabricated at the same time, such as may be accomplished using high strength nano-manufactured NiTi films of the type produced by Advanced Bio Prosthetic Surfaces Ltd. (ABPS) of San Antonio, Tex., for example. The support structures are generally configured to accommodate three leaflets; however, it is understood that the prosthetic heart valves delivered by the methods and delivery systems of the invention can incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets can be any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000:102: 813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Optional orientation and positioning of the stents using delivery systems of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. For example, when aligning stents with native anatomical structures using delivery systems of the invention, they should be aligned so as to not block the coronary arteries, and native mitral or tricuspid valves should be aligned relative to the anterior leaflet and/or the trigones/commissures.

The support structures of the stents can be wires formed from a shape-memory material such as a nickel titanium alloy (e.g., Nitinol). With such a shape-memory material, the support structure will be self-expandable from a contracted state to an expanded state, such as by the application of heat, energy, and the like, or by the removal of external forces (e.g., compressive forces of the type that can be provided by a moveable sheath). Such a support structure can preferably be repeatedly compressed and expanded without damaging the structure of the stent. In one embodiment, the support structure of such an embodiment may be cut (e.g., laser cut) from a single piece of material. In another embodiment, the support structure may be assembled from a number of different components. For these types of stent structures, one example of a delivery system that can be used includes a catheter with a retractable sheath that covers the stent until it is to be deployed, at which point the sheath can be retracted to allow the stent to expand.

The stents or support structures used with the delivery systems of the invention can alternatively include a series of wires or wire segments configured so that they are capable of transitioning from a collapsed state to an expanded state with the application or removal of external and/or internal forces. The wires comprising the support structure can be formed of a metal or other material. Further, the wires are arranged in such a way that the stent or support structure can be folded or compressed to a contracted state in which its internal diameter is considerably smaller than its internal diameter when the structure is in an expanded state. In its collapsed state, such a support structure with an attached valve can be mounted over a delivery device, such as a balloon catheter, for example. The support structure is configured so that it can be changed to its expanded state when desired, such as by the expansion of a balloon catheter or removal of external forces that are provided by a sheath, for example. The delivery systems used for such a stent can be provided with degrees of rotational and axial orientation capabilities in order to properly position the new stent at its desired location.

Figure 1:
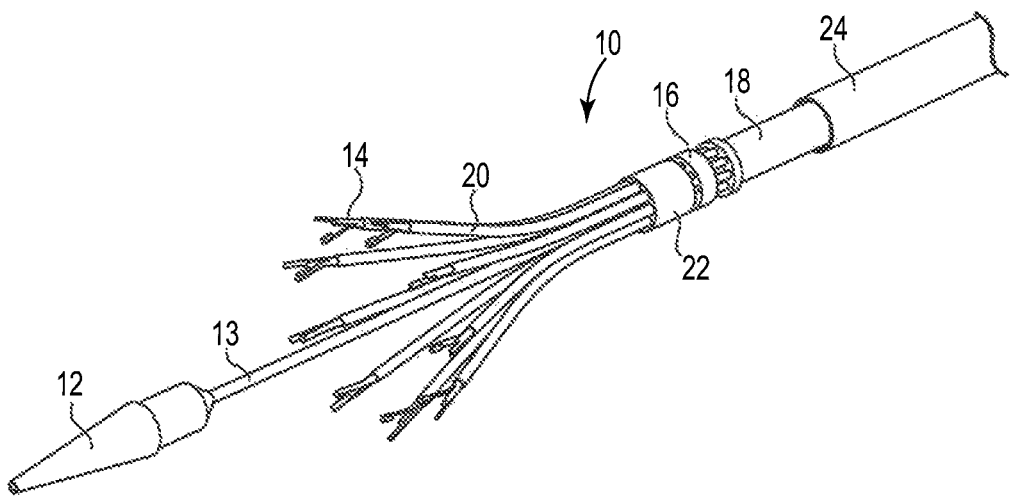
FIG. 1 is a perspective view of a distal end portion of an exemplary embodiment of a transcatheter stent or stented valve delivery system of the invention.

Referring now to the Figures, wherein the components are labeled with like numerals throughout the several Figures, and initially to FIG. 1, one embodiment of a delivery system 10 is illustrated, which can be used to deploy a stent, such as a valved stent, in a desired location in a patient. This delivery system allows a stent to be loaded and delivered to a desired location, then is used for at least partially deploying the stent, and then can optionally be used for recapturing the stent and relocating it, if desired. In general, delivery system 10 includes a distal tip 12 from which an elongated member 13 extends and an opposite proximal end that includes many of the control features for the delivery system. The distal tip 12 can provide a surface against which a sheath can be sealed, along with providing a sleeve actuation function, as will be described below.

Delivery system 10 further includes multiple capturing wires 14, each of which is attached to a wire connection member 16 at or near its proximal end. The outer surface of the member 16 may be sized and shaped to be cylindrical to generally match the inner size and shape of a sheath that will be slid over the member 16, as will be discussed in further detail below. It is understood, however, that the size and shape of the outer surface of member 16 can be differently configured.

In the illustrated embodiment, the capturing wires 14 are spaced from each other in a radial pattern to extend from the distal end of member 16, and in one particular embodiment, the delivery system 10 includes nine capturing wires 14 that are spaced evenly from each other (i.e., at approximately 40 degrees from each other) relative to the distal end of member 16. Such an embodiment would typically be used with a stent having nine crowns or attachments points, so that the number of capturing wires matches the number of crowns or attachment points of a corresponding stent. However, it is contemplated that the number of capturing wires 14 is different than the number of crowns or attachment points of a corresponding stent and/or that the number of capturing wires is more or less than nine. It is further contemplated that the capturing wires 14 are not evenly spaced from each other, but that some of the wires 14 are closer to adjacent wires 14 than others and/or that the wires 14 are spaced at either the same or different distances from an outer surface of the member 16. That is, the wires can be located at the same distance from a longitudinal axis of the delivery system, or can optionally be positioned at staggered distances from the longitudinal axis of the delivery system, such as to accommodate a stent that has a certain corresponding configuration. In any case, the assembly that is made up of the member 16 with extending capturing wires 14 can in turn be attached to an extension tube 18. The extension tube 18 can be attached to or extend from a handle (not shown) at its proximal end.

Each of the capturing wires 14 is at least partially surrounded by a sleeve 20 (shown enlarged in FIG. 9), wherein each of the sleeves 20 extends from, and/or can be attached to, a distal end of a sleeve connector member 22. As shown, connector member 22 is distal to wire connection member 16, wherein these members 16, 22 are spaced at different distances from each other depending on the deployment state of the delivery system. The outer surface of the member 22 may be sized and shaped to be cylindrical to generally match the inner size and shape of a sheath that will be slid over the member 22, as will be discussed in further detail below. It is understood, however, that the size and shape of the outer surface of member 22 can be differently configured.

The radial arrangement of the sleeves 20 relative to a distal end of connector member 22 is generally the same as the radial arrangement of the capturing wires 14 relative the distal end of member 16. Each of these sleeves 20 is positioned to enclose or partially enclose a corresponding capturing wire 14. Further, each of the sleeves 20 of this embodiment is axially slideable relative to its respective capturing wire 14. In one embodiment, the sleeves 20 are made of a flexible or semi-flexible material such that sliding of the sleeves relative to the capturing wires 14 does not change the formed shape of any of the capturing wires 14.

The delivery system 10 further includes a sleeve actuator that extends from the proximal end of the delivery system to the distal tip 12, which is attached to the connector member 22. The sleeve actuator at distal tip 12 can consist of a small tube that allows passage of a guide wire through it, along with a dilator tip at its distal end. The sleeve actuator can move freely relative to the extension tube 18, and can be affixed to an actuating mechanism (e.g., a drive screw, thumb slide, or the like) at its proximal end, such as sleeve actuator 84 of FIG. 11-14. This actuation mechanism can be attached within a handle at the proximal end of the delivery system 10, for example, in order to remotely control the axial movement of the sleeves 20 in their proximal and distal directions, as is illustrated in FIGS. 11-14, for example.

Figure 11:
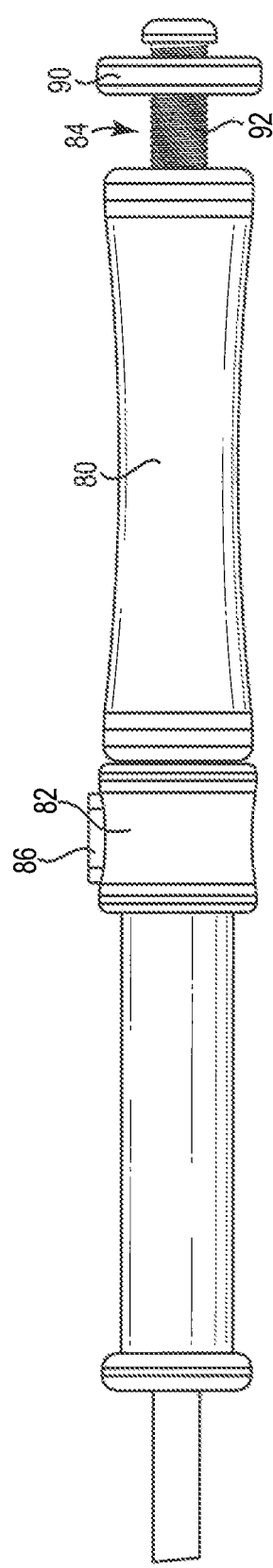
FIGS. 11-14 are front views of a proximal end of a delivery system of the invention, which illustrates exemplary sequential steps in the process of loading a stent onto the delivery system.

FIG. 11 illustrates a proximal end of a delivery system of the invention, which generally includes a handle body 80 that is attached to extension tube 18, along with a sheath actuator 82 that includes a thumb lock 86, and a sleeve actuator 84. In one embodiment, sleeve actuator 84 includes a knob 90 positioned on a threaded rod 92, as illustrated. One exemplary method of operating of these components of a delivery system is described in further detail below.

Referring again to FIG. 1, delivery system 10 further includes a sheath 24, which is sized to be able to surround the sleeves, capturing wires, and the connector members to which the sleeves and capturing wires are attached. Sheath 24 is axially moveable in a proximal and distal direction relative to the distal tip 12 via an actuating mechanism, such as sheath actuator 82 of FIGS. 11-14, for example. Such an actuator can be located at or near the proximal end of the delivery system to facilitate axial movement of the sheath. In one embodiment, the inner surface of the sheath 24 can be slightly larger than a proximal end of the distal tip 12 in order to be able to mate with it and completely encompass the various stent delivery components at the distal end of the device. In this way, the sheath 24 can help to provide a smooth surface for delivery of a stent through the vasculature of the patient.

Figure 2:
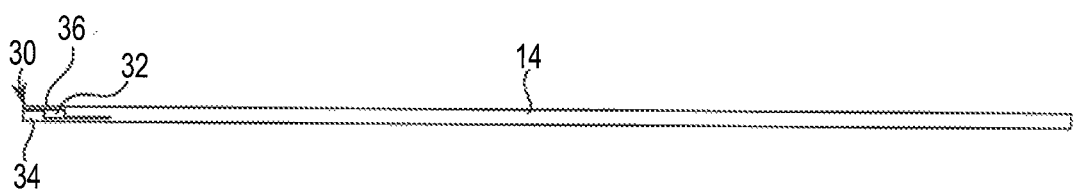
FIG. 2 is a side view of a capturing wire of the delivery system of FIG. 1, with its distal end in a closed position.
Figure 3:
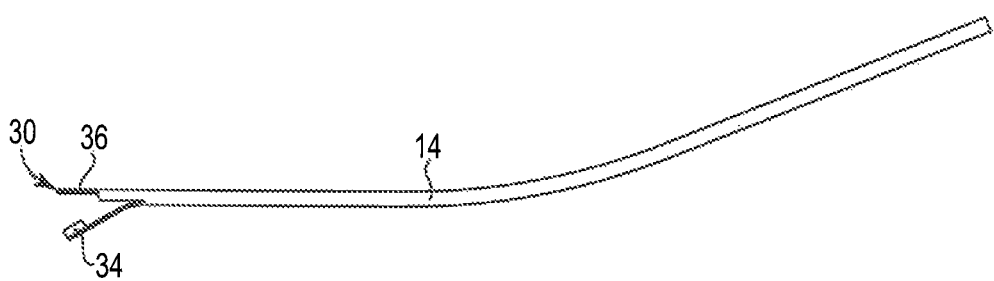
FIG. 3 is another side view of the capturing wire of FIG. 2, with its distal end in an open position.

FIGS. 2 and 3 illustrate one embodiment of a capturing wire 14 of a delivery system of the invention, such as delivery system 10. Capturing wire 14 is preferably an elongated piece of a shape-memory material, such as Nitinol, having a distal end 30 that is configured for attachment to a stent frame. FIG. 2 illustrates this capturing wire 14 in a "closed" configuration in which its distal end 30 has been cut or otherwise formed into multiple sections or pieces, such as can be performed using laser cutting techniques, EDM, and the like. FIG. 3 illustrates the same wire 14 after it has been placed in a forming fixture or otherwise manipulated to provide a certain bent or curved wire configuration, such as the relatively curved shape shown. Distal end 30 of wire 14 includes an opening or slot 32, which is positioned between a lower portion 34 and an upper portion 36. Upper portion 36 can be generally fixed to extend in the same general direction as the longitudinal axis of the wire 14, as shown, although it can instead be configured so that it extends in a different direction (e.g., bent or curved) relative to the longitudinal axis of the wire 14. Lower portion 34 is moveable relative to the upper portion 36 so that extends in a direction that is generally not parallel to the longitudinal axis of the wire 14 and the upper portion 36, as is shown in FIG. 3. As is further illustrated in FIG. 3, capturing wire 14 is bent or angled along its length, wherein the particular angle of the sections of the wire relative to each other is selected for engagement with a stent having a certain configuration, as is explained below relative to an exemplary process of capturing, delivering, and deploying an expandable stent.

The configuration for the distal end 30 of the capturing wires 14 illustrated herein is one exemplary wire embodiment, wherein it is understood that the distal end 30 may be configured differently than shown, while remaining within the scope of the invention. That is, the distal end can include a slot or opening that is larger or smaller than shown, or that has a different shape than the illustrated rectangular slot shape, such as circular or contoured. In any case, the configuration of this distal end desirably will provide for both secure capture of the stent structure along with relatively easy release of the stent from the delivery system, when desired. Thus, the slot or opening in one embodiment can be at least slightly larger than the outer size and shape of the stent wire that it will be capturing in order for the upper and lower portions to completely enclose the wire crowns of a stent. However, the slot or opening in the end of the capturing wire 14 may instead be smaller than the wire of the stent with which it will be engaged.

Figure 4:
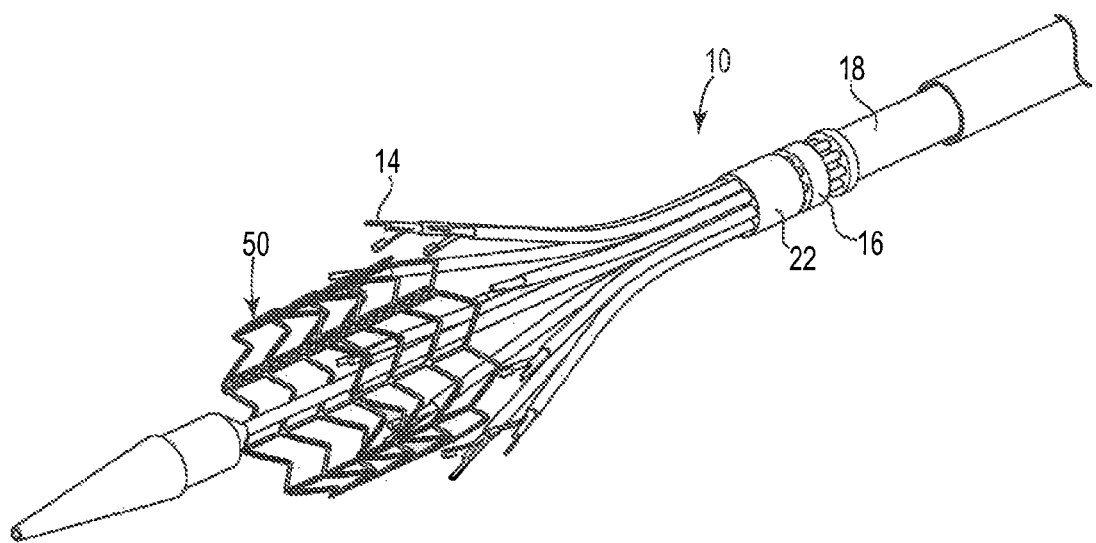
FIG. 4 is a perspective view of one step of loading a stent onto a distal end portion of a transcatheter delivery system of the invention, wherein the stent is not yet positively engaged with the capturing wires.

FIGS. 4-8 illustrate multiple sequential steps of an exemplary process of loading a stent 50 onto the delivery system 10 described above, although it is understood that the delivery system 10 can deliver stents having a different configuration than is illustrated in these figures. In any case, the stent 50 includes a series of wires or wire segments arranged so that they are capable of transitioning from a collapsed state to an expanded state, as described above, and preferably is a self-expanding stent comprising a shape-memory material. Delivery system 10 can be prepared for loading stent 50 thereon by first positioning the stent 50 in its expanded or semi-expanded condition generally at the distal end of the delivery system 10 and over its distal tip 12, as is illustrated in FIG. 4. At this point, the components at the proximal end of the delivery system can generally be positioned as shown in FIG. 11, for example, with the sheath actuator 82 at a generally proximal location (i.e., adjacent to handle body 80) and the knob 90 proximally positioned along threaded section 92 (i.e., relatively close to the proximal end of the delivery system and spaced from the handle body 80). In this position, the proximal end of stent 50 is located generally adjacent to the distal end of the capturing wires 14, wherein the lower and upper portions 34, 36 of each wire 14 are moveable relative to each other to allow access to the opening or slot 32 between them.

Figure 5:
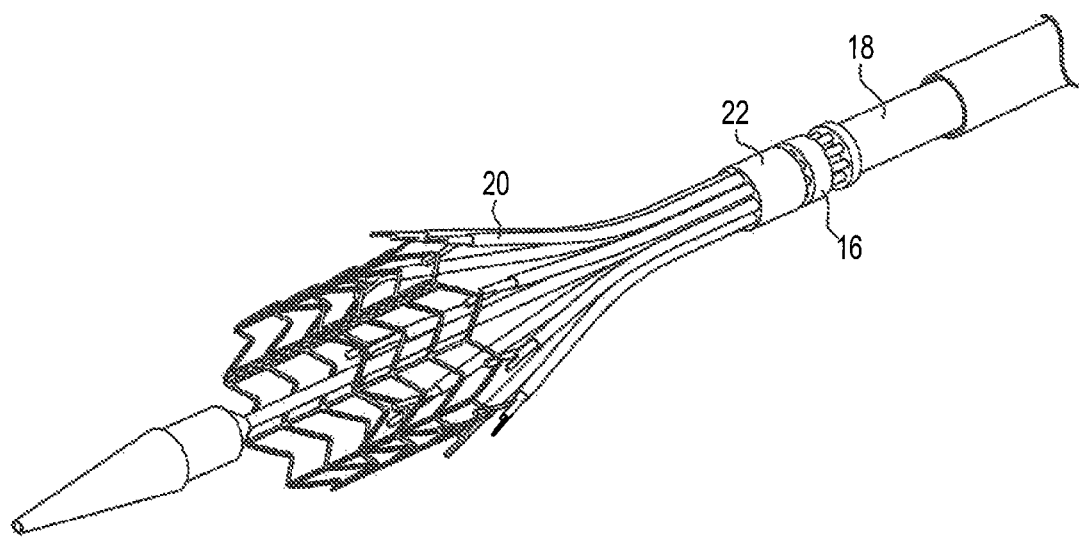
FIGS. 5-7 are perspective views of three sequential steps of loading a stent onto the distal end portion of the delivery system of FIG. 1, which illustrates the stent as it is positively engaged with capturing wires.
Figure 15:
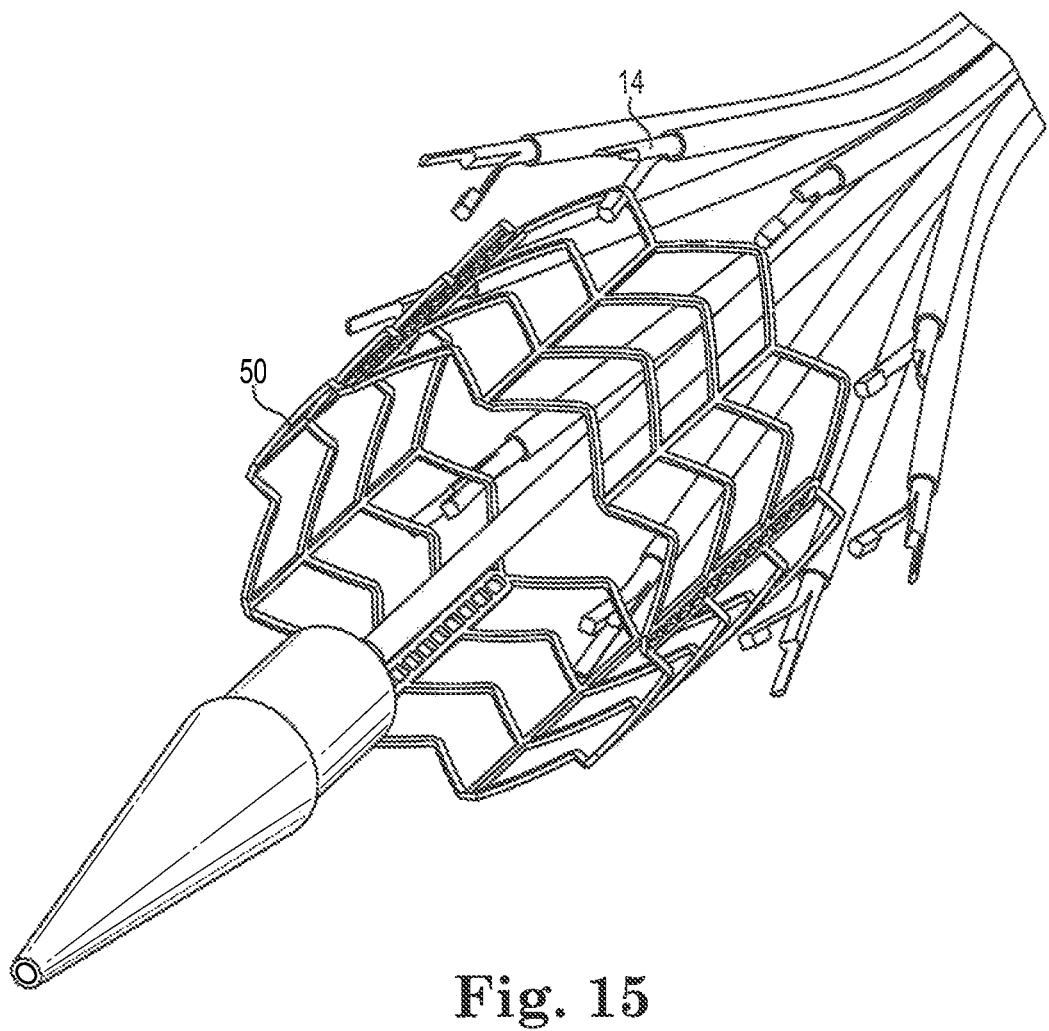
FIGS. 15-17 are perspective views of capturing wires of a delivery system adjacent to wires of a stent.
Figure 16:
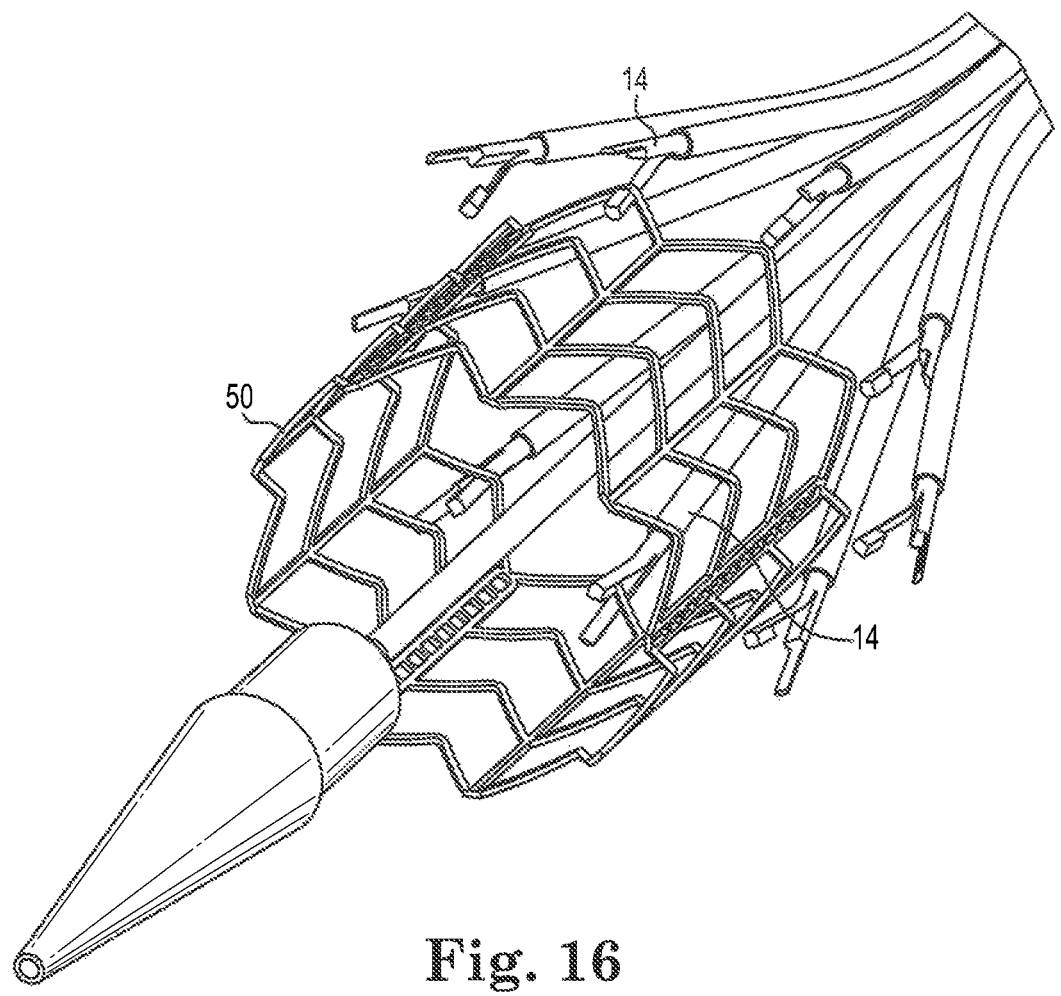
Figure 17:
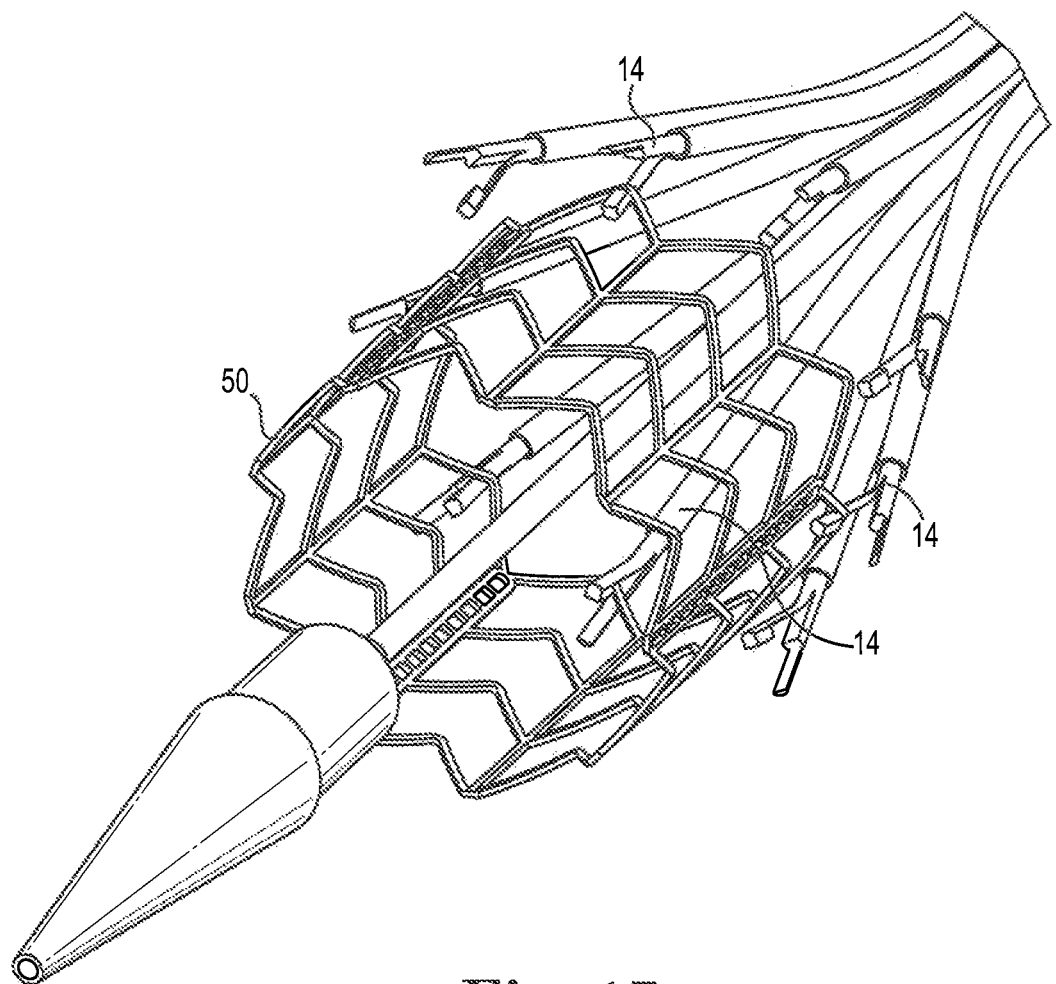

Next, a single crown of the stent 50 is positioned within one of the slots 32, as is illustrated in FIG. 15. In particular, one crown of stent 50 is placed between the lower and upper portions 34, 36 of one of the wires 14. An additional capturing wire 14 can be hooked onto a crown of the stent 50, as is illustrated in FIG. 16. This second wire 14 can be located at approximately 160 degrees from the first wire 14, for example, which is located on the approximate opposite side of the stent for a nine crown stent. Such a loading sequence is optional, but can provide for additional stability in the stent-loading process. This second wire 14 can then be compressed inwardly while the lower portion 34 of the wire 14 is positioned relative to the corresponding crown of stent 50. The outward spring force of the wire 14 acts to lock the raised area of the lower portion 34 into the crown of the stent 50. Next, a third wire 14 can be hooked onto another crown of the stent 50, as is illustrated in FIG. 17, which may be selected from any of the remaining wires 14 that are not yet attached to a stent crown. The attachment of the third wire 14 tends to further stabilize the stent 50 relative to the distal end of the wires. The remaining wires 14 can then be hooked onto the remaining stent crowns, as is illustrated in FIG. 5.

Figure 6:
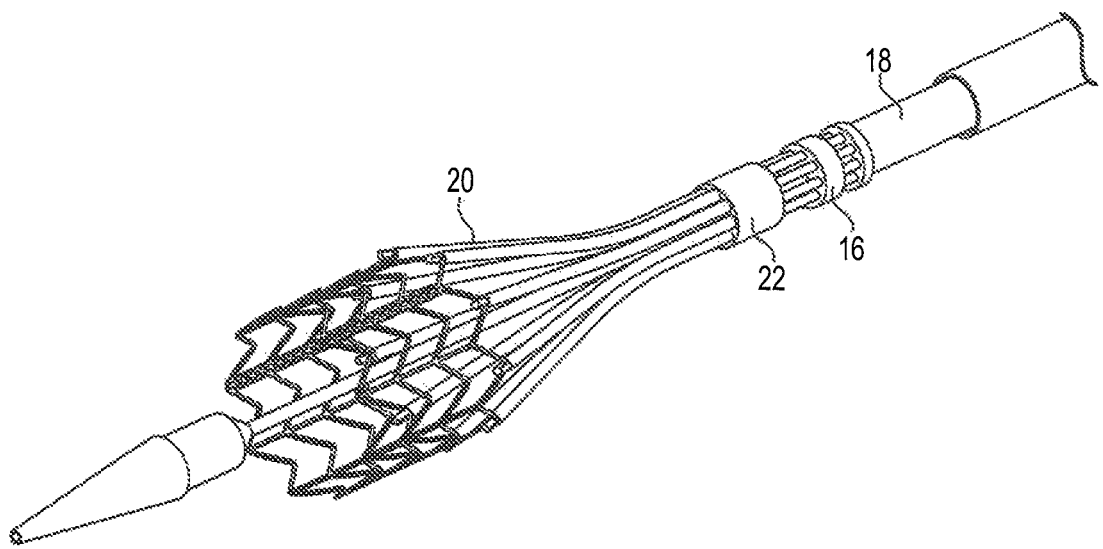
Figure 12:
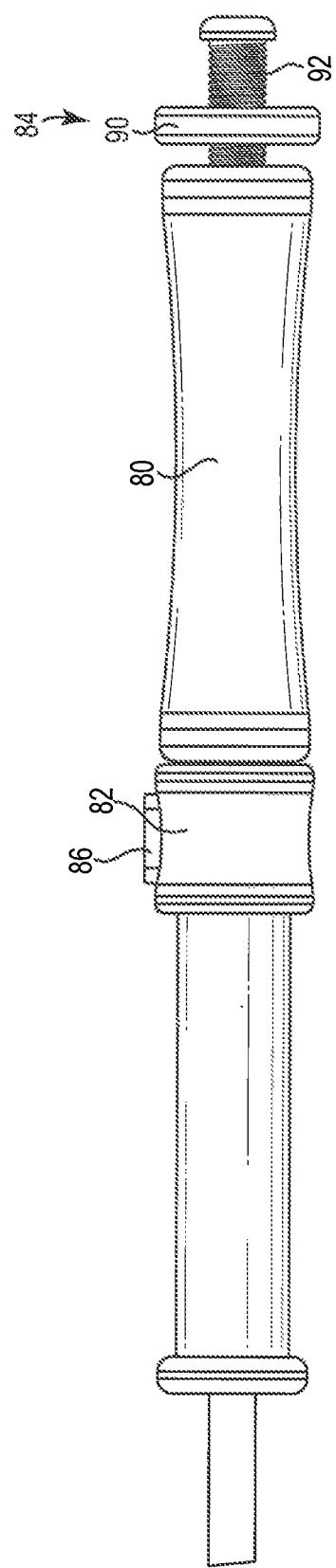

The next step of loading stent 50 onto delivery system 10 is illustrated in FIG. 6 and includes moving the sleeves 20 toward the distal ends of the capturing wires 14 via a mechanism at the proximal end of the delivery system. In particular, the knob 90 of sleeve actuator 84 is rotated to advance it along the threaded section 92, as is shown in FIG. 12, thereby advancing the sleeves 20 in a distal direction. As the sleeves 20 are moved closer to the distal ends 30 of capturing wires 14, the upper and lower portions 34 and 36 will be pressed toward each other and toward the stent wire that is positioned between them. In this embodiment, the elongated member 13 is attached to the sleeve cylinder 22, which in turn is attached to the knob 90 of sleeve actuator 84. It is possible that the system is configured so that the distal tip 12 does not move when advancing the sleeves 20. Referring again to FIG. 6, the sleeve cylinder 22 is now spaced further from the adjacent connection cylinder 16 and closer to the distal tip 12. This movement locks the stent crowns in place relative to the distal ends 30 of the capturing wires 14 by forcing the lower and upper portions 34, 36 of wires 14 together.

Figure 7:
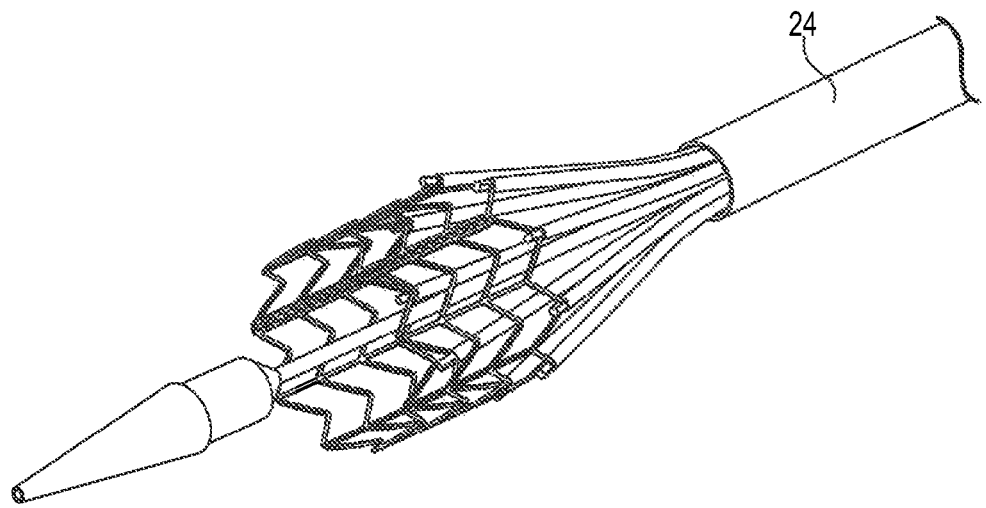
Figure 13:
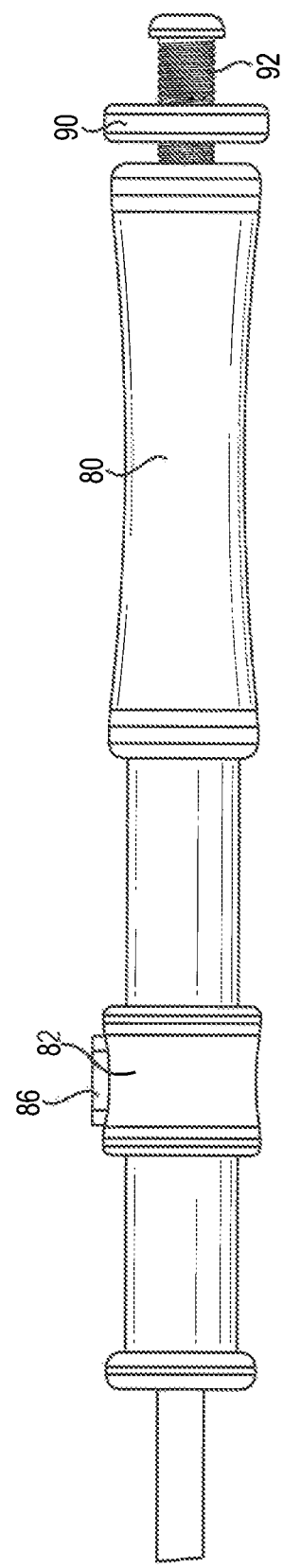

Next, sheath 24 is moved in a distal direction toward the distal tip 12 to compress the stent structure and surround the stent 50 and the mechanisms that are attaching the stent to the delivery system 10. This may be accomplished by depressing the thumb lock 86 to allow the sheath actuator 82 to slide forward, as is illustrated in FIG. 13. Because the sheath 24 is attached to the sheath actuator 82, this movement of the actuator 82 causes the corresponding movement of the sheath 24 toward the distal tip 12, as is illustrated in FIG. 7. Further movement of the sheath 24 in a distal direction will compress the capturing wires 14 toward a longitudinal axis of the delivery system, which will force them against their outward bias or splaying, as illustrated and described herein.

Figure 8:
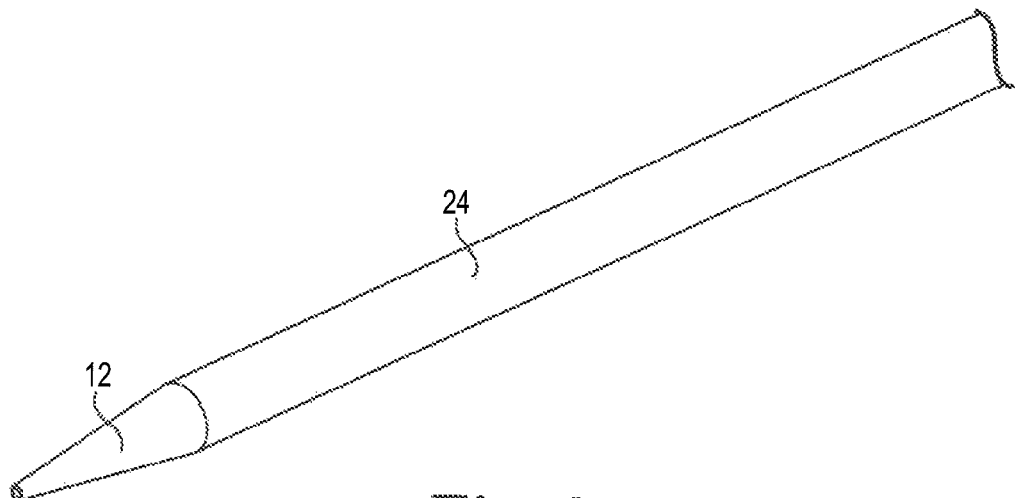
FIG. 8 is a perspective view of a delivery system of the invention, such as it can be configured when a stent is fully captured within a sheath.
Figure 14:
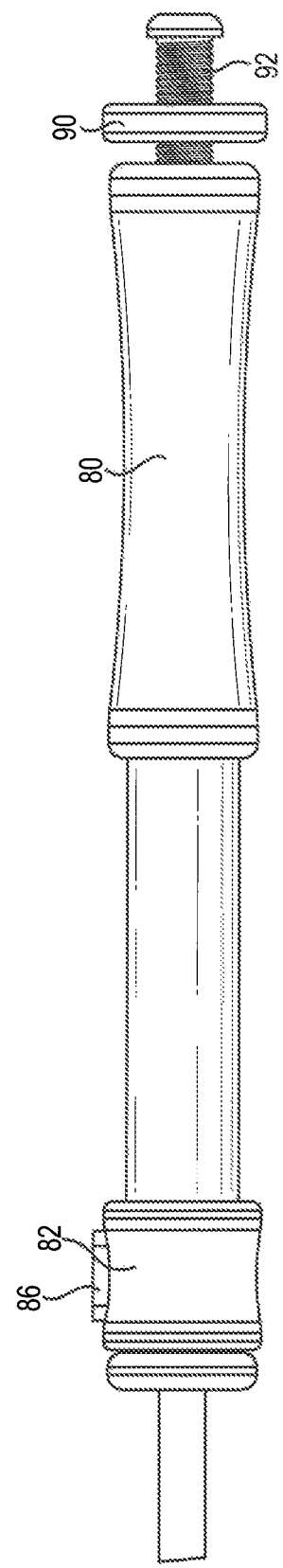

FIG. 8 illustrates one exemplary position of the delivery system 10 with a stent in its fully loaded condition, where the sheath 24 has been moved all the way to the distal tip 12 so that the stent 50 and components used to attach it to the delivery system are all enclosed within the sheath 24. An exemplary corresponding position of the sheath actuator 82 relative to the handle body 80 is illustrated in FIG. 14, where the actuator 82 is located at its furthest distance from the handle body 80 when the sheath 84 is moved to its most distal location relative to distal tip 12.

It is understood that while the distal end features of the capturing wires described herein are generally shown to be engaging with the end crowns of a stent, the distal end features can additionally or alternatively engage with intermediate stent crowns or other stent features.

Figure 9:
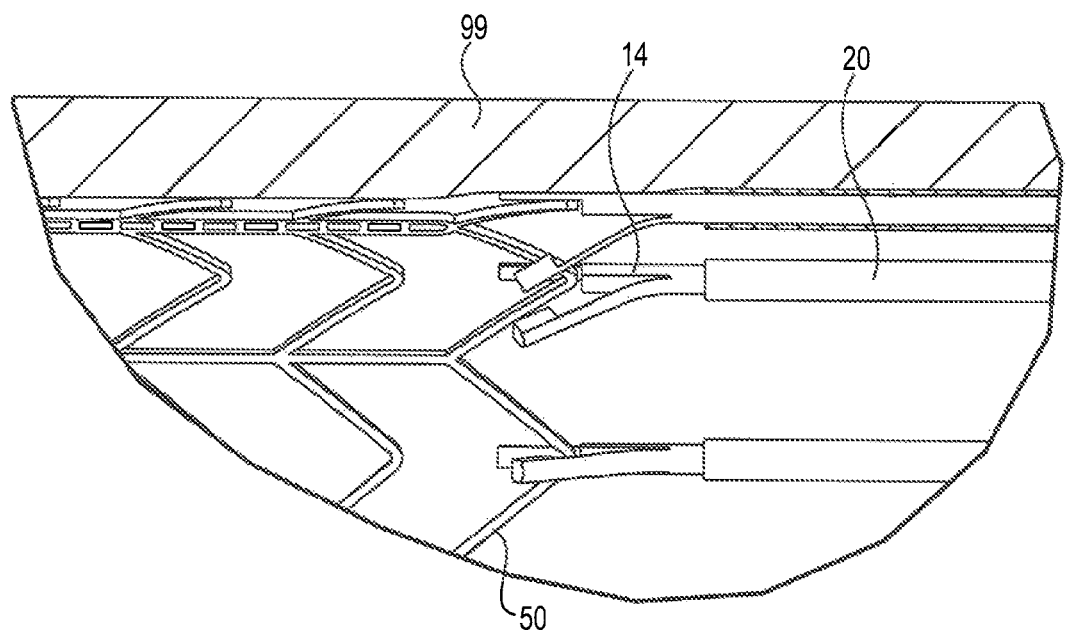
FIG. 9 is an enlarged front view of a portion of a stent adjacent to the distal ends of the capture wires of a delivery system.
Figure 18:
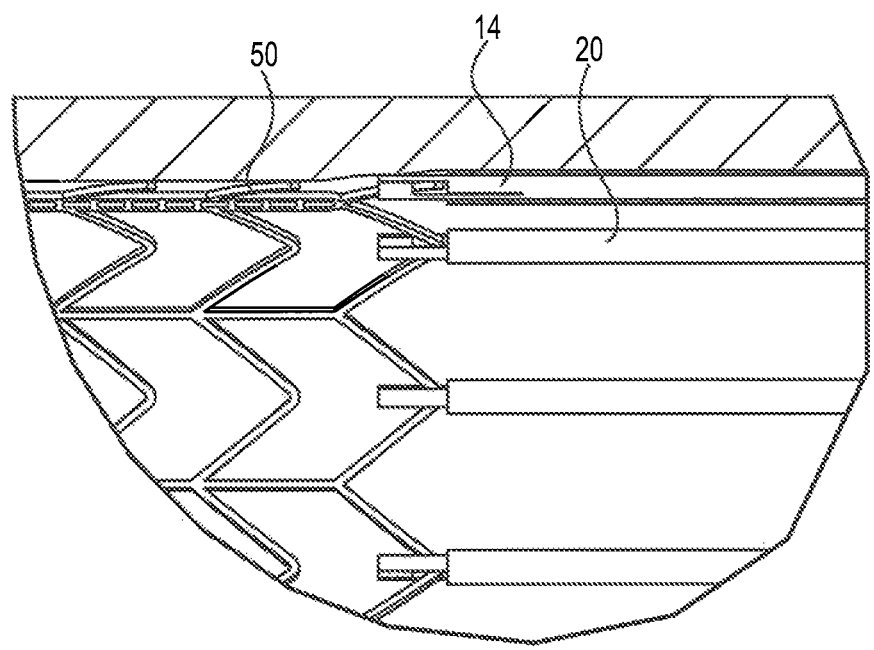
FIGS. 18 and 19 are front enlarged views of a portion of a stent as it is being released from the distal ends of capturing wires of a delivery system.

After the stent 50 is loaded onto the delivery system 10 and enclosed within the sheath 24, as illustrated in FIG. 8, the delivery system can be inserted into the desired stent deployment location with the patient (e.g., the area adjacent to the native aortic valve). In order to deploy the stent after it has been properly positioned in the patient, the sheath 24 can be pulled back to expose the stent 50 and the capturing wires 14 engaged with the crowns of the stent 50, as is illustrated in FIG. 18. In particular, FIG. 18 illustrates the position of the delivery system components, such as the sleeves 20, relative to the stent 50 just prior to the configuration shown in FIG. 9. It is noted that at the point in the process illustrated in FIG. 18, the stent (and valve) could be pulled back into the sheath and repositioned within the patient, if desired. However, once the user is satisfied with the position of the stent, the sleeves 20 can be retracted even further to allow the distal ends of the wires 14 to open, thereby releasing the stent 50 completely. That is, the sleeves 20 can be retracted by moving the sleeve cylinder 22 in a proximal direction relative to the ends of the capturing wires 14. The capturing wires 14 are designed so that when positioned in a desired deployment location, retracting the sleeves 20 will cause the lower portions 34 of the capturing wires 14 to pull away or disengage from the stent crowns because the upper portions 36 rest against the vessel wall 99, thereby releasing the stent from the capturing wires 14, as is illustrated in FIG. 9.

Figure 19:
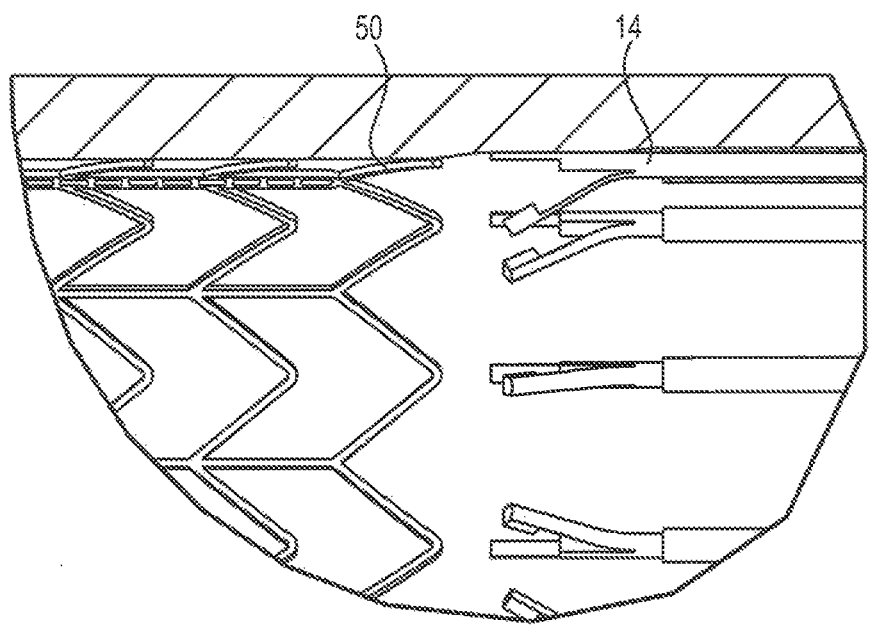

At this point, the stent 50 can be considered to be deployed in its implantation location, such that the delivery system can then be moved in a proximal direction until the distal ends 30 of the capturing wires 14 are clear of the stent, as shown in FIG. 19. If desired, the sheath 24 can then be moved back toward the distal tip 12 of the delivery system 10 to enclose the wire connection components, which can help to prevent possible undesirable interference between the capturing wires 14 and the stent or surrounding tissue of the patient. The delivery system 10 can then be removed from the patient.

The present invention has now been described with reference to at least one embodiment thereof. The contents of any patents or patent application cited herein are incorporated by reference in their entireties. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A delivery system for delivery of an implantable stented device to a body lumen, the delivery system including a distal end and a proximal end and comprising:
   a handle adjacent the proximal end of the delivery system;
   a wire connection member positioned between the distal end of the delivery system and the handle;
   a plurality of capturing wires fixedly attached to the wire connection member and extending from a distal end of the wire connection member, each of the capturing wires having a distal end having a lower portion that is moveable relative to an upper portion between an open position and a closed position, and a slot defined by the upper portion and the lower portion in the closed position, the lower portion and the upper portion being integrally formed and extending from a proximal juncture of the distal end of the capturing wire;
   a plurality of sleeves, wherein each of the plurality of sleeves surrounds one of the capturing wires; and a sleeve connection member positioned between the wire connection member and the distal end of the delivery system, wherein each of the sleeves is fixedly attached to the sleeve connection member and extends from a distal end of the sleeve connection member, and wherein the sleeve connection member is axially translatable to move the sleeves axially relative to their respective capturing wires.

2. The delivery system of claim 1, wherein each of the sleeves is slideable along at least a portion of a length of its respective capturing wire.

3. The delivery system of claim 2, wherein each of the sleeves is tubular and comprises an internal opening that is positionable to surround the distal end of its respective capturing wire when the upper and lower portions are in their closed position.

4. The delivery system of claim 1, further comprising a sheath that is slideable relative to the wire connection member, wherein the sheath comprises an internal area for surrounding the plurality of capturing wires and the wire connection member.

5. The delivery system of claim 1, wherein each of the capturing wires comprises a shape-memory material.

6. The delivery system of claim 1, wherein the plurality of capturing wires are spaced from each other in a radial pattern relative to the distal end of the wire connection member.

7. The delivery system of claim 1, wherein each of the capturing wires comprises a formed shape so that it flares outwardly relative to a longitudinal axis of the delivery system when in an uncompressed condition.

8. The delivery system of claim 7, further comprising a slideable sheath having an internal area for compressing the wires toward the longitudinal axis of the delivery system and at least partially surrounding the plurality of capturing wires.

9. The delivery system of claim 1, wherein the upper portion, lower portion, and slot of each of the capturing wires are formed using laser cutting techniques.

10. The delivery system of claim 1, wherein the lower portion and the upper portion of each of the capturing wires are biased away from each other when not subjected to externally applied forces.

11. The delivery system of claim 1, in combination with a self-expandable stented device that is transitionable from a collapsed state to an expanded state with the removal of an externally applied force.

12. The delivery system of claim 11, wherein the stented device includes a plurality of wire crowns, wherein each of the crowns is engageable with the distal end of one of the capturing wires.

13. A delivery system for delivery of an implantable stented device to a body lumen, the delivery system including a distal end and a proximal end and comprising:
   a handle adjacent the proximal end of the delivery system;
   a wire connection member positioned between the distal end of the delivery system and the handle;
   a plurality of capturing wires fixedly attached to the wire connection member and extending from a distal end of the wire connection member, each of the capturing wires having a distal end having a lower portion that is moveable relative to an upper portion between an open position and a closed position, and a slot defined by the upper portion and the lower portion in the closed position, the lower portion and the upper portion being integrally formed and extending from a proximal juncture of the distal end of the capturing wire; and
   a plurality of sleeves, wherein each of the plurality of sleeves surrounds one of the capturing wires;
   wherein a proximal end portion of the delivery system comprises:
   a sheath actuator for controlling slideable movement of a sheath relative to the wire connection member; and
   a sleeve actuator for controlling slideable movement of the plurality of sleeves.

14. The delivery system of claim 13, wherein the sleeve actuator comprises a threaded rod and a knob that is rotatable along the threaded rod to simultaneously axially move each of the plurality of sleeves relative to the distal end of its respective capturing wire.

15. The delivery system of claim 13, wherein the sheath actuator comprises a locking mechanism that is releasable to allow axial movement of the sheath actuator relative to the wire connection member.

* * * * *